United States Patent
Mowli et al.

(10) Patent No.: US 9,664,685 B2
(45) Date of Patent: May 30, 2017

(54) METHODS FOR ANALYSIS OF PROTAMINE

(71) Applicant: Fresenius Kabi USA, LLC, Lake Zurich, IL (US)

(72) Inventors: Jay Mowli, Chicago, IL (US); Pearle Torralba, Chicago, IL (US); Kamlesh Patel, Streamwood, IL (US)

(73) Assignee: Fresenius Kabi USA, LLC, Lake Zurich, IL (US)

( * ) Notice: Subject to any disclaimer, the term of this patent is extended or adjusted under 35 U.S.C. 154(b) by 263 days.

(21) Appl. No.: 14/055,625

(22) Filed: Oct. 16, 2013

(65) Prior Publication Data

US 2015/0104785 A1    Apr. 16, 2015

(51) Int. Cl.
*C12Q 1/44* (2006.01)
*C12Q 1/37* (2006.01)
*G01N 33/68* (2006.01)

(52) U.S. Cl.
CPC .................... *G01N 33/68* (2013.01)

(58) Field of Classification Search
CPC ..................................... G01N 33/68
USPC ..................................... 435/19, 23
See application file for complete search history.

(56) References Cited

PUBLICATIONS

Sadowski et al. (Journal of Biological Chemistry, vol. 247, No. 2, p. 405-412, 1972).*
Tzan et al. (Journal of Membrane Biology, vol. 133, p. 227-242, 1993).*
Mesbah et al. (International Journal of Systematic Bacteriology, p. 159-167, 1989).*
Tortorella et al. Proteolytic Release and Partial Characterization of Human Sperm-Surface Glycopeptides; Brazilian Journal of Medical and Biological Research, vol. 30 (1997) pp. 387-393.*
Wang et al. Ultra-Performance Liquid Chromatography/Tandem Mass Spectrometry for Accurate Quantification of Global DNA Methylation in Human Sperms; Journal of chromatography B, vol. 879 (2011) pp. 1647-1652.*
Lee et al. Successful Treatment of Anaphylactic Shock After Protamine Administration—Report of a Case; Emergency Medicine, vol. 3, No. 5 (2013) pp. 1-3.*
Sipos et al. An Effect of Calcium Ions on the Activity, Heat Stability, and Structure of Trypsin; Biochemistry, vol. 9, No. 14 (1970) pp. 2766-2775.*
Gill et al., "Purification and Analysis of Protamine," *Process Biochemistry*, 41: 1875-1882 (2006).
Hoffmann et al., "Purification and Analysis of the Major Components of Chum Salmon Protamine Contained in Insulin Formulations Using High-Performance Liquid Chromatography," *Protein Expression and Purification*, 1: 127-133 (1990).
Awotwe-Otoo et al., "Application of quality by design elements for the development and optimization of an analytical method for protamine sulfate," *Journal of Pharmaceutical and Biomedical Analysis 62*, pp. 61-67 (2012).
Hoffmann et al., "Purification and Analysis of the Major Components of Chum Salmon Protamine Contained in Insulin Formulations Using High-Performance Liquid Chromatography," *Protein Expression and Purification 1*, pp. 127-133 (1990).
Hvass A et al., "Determination of protamine peptides in insulin drug products using reversed phase high performance liquid chromatography," *Journal of Pharmaceutical and Biomedical Analysis 37*, pp. 551-557 (2005).
Federal Institute of Industrial Property, International Search Report in International Application No. PCT/US2014/060444 (Jan. 29, 2015).

* cited by examiner

*Primary Examiner* — Scott Long
*Assistant Examiner* — Paul Martin
(74) *Attorney, Agent, or Firm* — Leydig, Voit & Mayer, Ltd.

(57) ABSTRACT

The invention provides a method for analyzing a protamine sample for the presence or amount of at least one nucleotidic impurity. The invention also provides a method for the quantitation of peptides in a sample of protamine comprising four major peptides and at least one related impurity.

8 Claims, 6 Drawing Sheets

METHODS FOR ANALYSIS OF PROTAMINE

BACKGROUND OF THE INVENTION

Protamines are simple proteins of low molecular weight that are rich in arginine and strongly basic. Protamines are extracted from the sperm of salmon and other fish species.

Protamine sulfate occurs as a fine white, or off white, amorphous or crystalline powder. It is sparingly soluble in water. The pH of protamine sulfate in solution is between 6.0 and 7.0. It is used to bind with heparin in the body. The cationic protamine at a pH of 6.8 to 7.1 reacts with anionic heparin at a pH of 5.0 to 7.5 to form an inactive complex.

Protamine sulfate may be supplied as a sterile, isotonic solution for administration to patients. It acts as a heparin antagonist and is also a weak anticoagulant.

When supplied as a pharmaceutical active ingredient, protamine sulfate contains four major peptides and other related peptides (or possible impurities). Presently, there are no reference standards available (including impurity standards). In addition, protamine sulfate may contain impurities in the form of nucleotides that in turn may derive from DNA present in the sample.

It is necessary to characterize protamine sulfate in order to satisfy various regulatory requirements before use in humans and other animals. Presently, there are no reference standards of the four major peptides comprising protamine sulfate or of related peptides or possible impurities. Thus, there remains in the art a need for improved methods for the analytical characterization of protamine sulfate.

BRIEF SUMMARY OF THE INVENTION

The invention provides a method for analyzing a protamine sample for the presence or amount of at least one nucleotidic impurity, comprising the steps of (a) providing a protamine sample, (b) subjecting the sample of protamine to disruption with a protamine-disrupting agent to provide a first mixture, (c) subjecting the first mixture to a digestion step to provide a second mixture, and (d) determining the presence or amount of the at least one nucleotidic impurity present in the second mixture.

The invention also provides a method for analyzing a sample of protamine comprising four major peptides corresponding to Peptides 1-4 in FIG. 1 and at least one related impurity, comprising (a) subjecting a solution of the sample of protamine to a high pressure liquid chromatography (HPLC) under conditions suitable to resolve the four major peptides and at least one related impurity in a chromatogram, (b) determining the areas under the peaks of the four major peptides in the chromatogram, (c) determining the area under the peak of the at least one related impurity in the chromatogram, and (d) determining the concentration of (i) one or more of the four major peptides, (ii) the sum of two or more of the four major peptides, and/or (iii) the at least one related impurity.

BRIEF DESCRIPTION OF THE SEVERAL VIEWS OF THE DRAWING(S)

FIG. 1 depicts a high pressure liquid chromatogram of a sample of protamine sulfate analyzed in accordance with an embodiment of the invention.

FIG. 2 depicts representative chromatograms of Nucleoside Identification Solution showing nucleotidic impurities of DNA and RNA (FIG. 2A); Protamine Sulfate, USP Raw Material from Source 1 (FIG. 2B); Protamine Sulfate, USP Raw Material from Source 2 (FIG. 2C); and Protamine Sulfate, USP Raw Material from Source 3 (FIG. 2D).

DETAILED DESCRIPTION OF THE INVENTION

Figure 1:
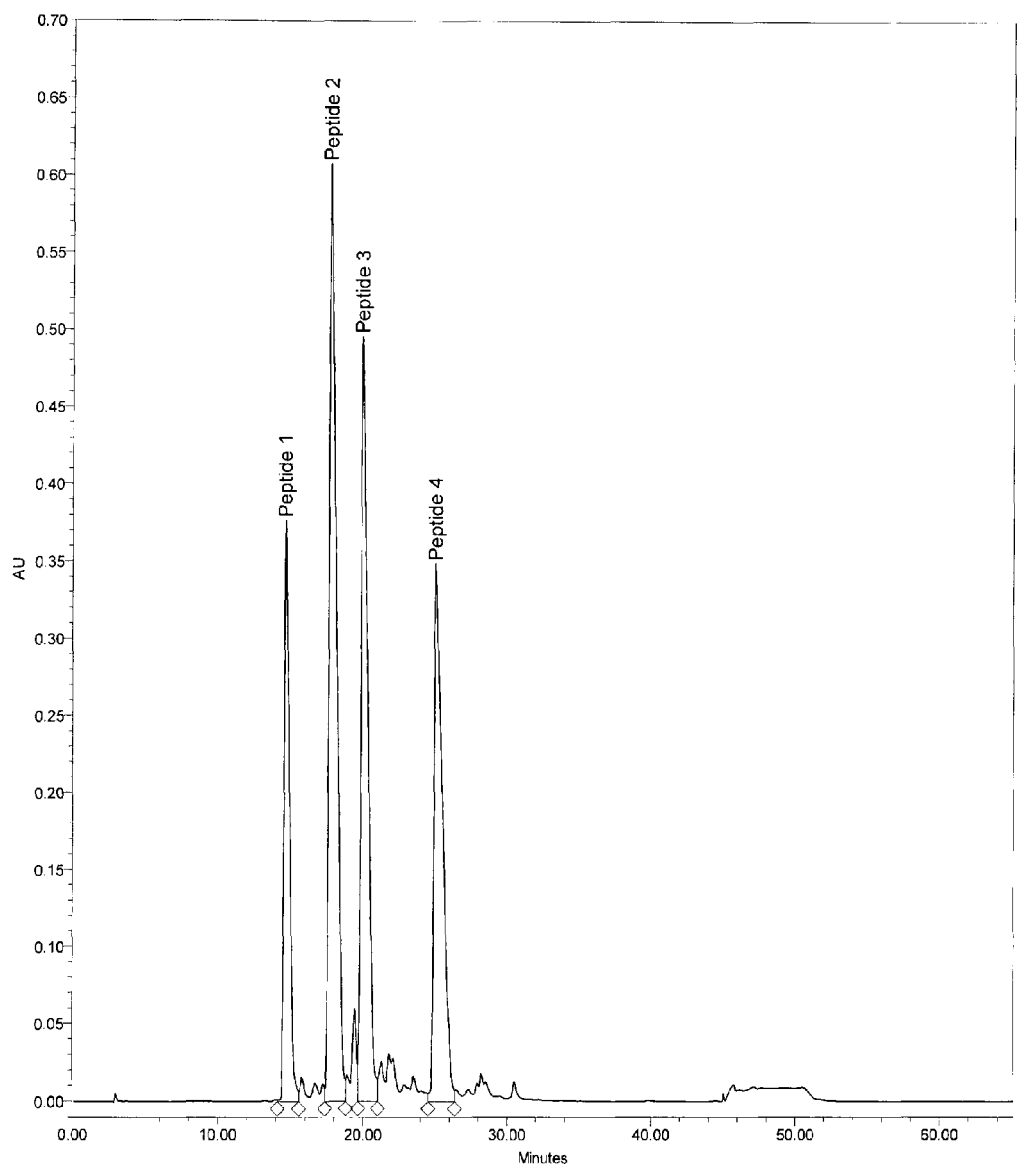

In an embodiment, the invention provides a method for analyzing a protamine sample for the presence or amount of at least one nucleotidic impurity, comprising the steps of (a) providing a protamine sample, (b) subjecting the sample of protamine to disruption with a protamine-disrupting agent to provide a first mixture, (c) subjecting the first mixture to a digestion step to provide a second mixture, and (d) determining the presence or amount of the at least one nucleotidic impurity present in the second mixture.

In any of the embodiments of the methods described herein, the protamine can be derived from a natural source, such as the sperm of salmon or another species of fish, or the protamine can be produced recombinantly. The term "protamine" includes protamine salts, such as protamine sulfate and protamine hydrochloride.

The term "nucleotidic impurity" refers to any compound derived from a preparation of nucleic acids. In certain embodiments, the nucleotidic impurity in the protamine sample is associated with the presence of DNA. In some embodiments, the nucleotidic impurity is a single- or double-stranded oligonucleotide, a nucleotide, a nucleoside, or a nucleobase. Exemplary nucleotidic impurities include, without limitation, adenosine, deoxyadenosine, guanosine, deoxyguanosine, cytidine, deoxycitidine, thymidine, uridine, and methylated or phosphorylated derivatives of the foregoing.

The protamine disrupting agent can be any agent capable of disrupting the binding between protamine and nucleic acids. In one embodiment, the protamine disrupting agent is a protease, such as a serine protease.

In a particular embodiment, the protamine-disrupting agent is trypsin. The trypsin can be immobilized, e.g., on a silica stationary phase or on magnetic beads, or the trypsin can be free in solution. In certain embodiments, the trypsin is inactivated prior to the digestion step. The trypsin can be inactivated by heat treatment, or by use of a chemical inhibitor of trypsin.

In another embodiment, the protamine disrupting agent is a strongly charged chemical reagent. In one embodiment, the protamine disrupting agent is a positively charged chemical reagent, such as spermine, spermidine, arginine, poly-arginine, or poly-lysine. In another embodiment, the protamine disrupting agent is a negatively charged chemical reagent, such as aspartate or heparin.

In yet another embodiment, the protamine disrupting agent is a physical treatment, such as heating or sonication.

In still yet other embodiments, the protamine disrupting agent is a solid phase extraction material, such as a strong cation exchange resin.

In any of the above embodiments, prior to step (c) the first mixture can be heated under conditions sufficient to inactivate the protamine-disrupting agent. The presence of the protamine-disrupting agent may interfere with the digestion step. Thus, in certain embodiments, the protamine-disrupting agent may be inactivated by heating. For example, the first mixture can be heated to a temperature of about 30° C. or more, about 40° C. or more, about 50° C. or more, about 60° C. or more, about 70° C. or more, about 80° C. or more, about 90° C. or more, or about 100° C. or more.

In any of the above embodiments, the digestion step comprises subjecting the first mixture to digestion with an endonuclease, a phosphodiesterase, an alkaline phosphatase, or combinations thereof to provide the second mixture. The endonuclease, phosphodiesterase, and alkaline phosphatase can be any suitable endonuclease, phosphodiesterase, or alkaline phosphatase. In certain embodiments, the endonuclease is an endonuclease derived from *Serratia marcescens*. An example of a suitable endonuclease is BENZONASE™ endonuclease (EMD Millipore, Billerica, Mass.), which is a genetically engineered endonuclease derived from *Serratia marcescens* that is produced and purified from *E. coli* strain W3110. In certain embodiments, the phosphodiesterase is phosphodiesterase I.

In one embodiment of the invention, the digestion step comprises subjecting the first mixture to digestion with an endonuclease, a phosphodiesterase and an alkaline phosphatase. Preferably, the digestion step comprises subjecting the first mixture to digestion with an endonuclease from *Serratia marcescens*, phosphodiesterase I, and an alkaline phosphatase.

In any of the above embodiments, the step of determining the presence or amount of at least one nucleotidic impurity present in the second mixture can comprise subjecting the second mixture to a high pressure liquid chromatography to obtain a chromatogram, and comparing at least one peak obtained in the chromatogram due to the presence of at least one nucleotidic impurity to at least one peak resulting from a chromatogram obtained from a reference standard of the at least one nucleotidic impurity.

In another embodiment, the invention provides a method for analyzing a sample of protamine comprising four major peptides corresponding to Peptides 1-4 in FIG. 1 and at least one related impurity, comprising (a) subjecting a solution of the sample of protamine to a high pressure liquid chromatography (HPLC) under conditions suitable to resolve the four major peptides and at least one related impurity in a chromatogram, (b) determining the areas under the peaks of the four major peptides in the chromatogram, (c) determining the area under the peak of the at least one related impurity in the chromatogram, and (d) determining the concentration of (i) one or more of the four major peptides, (ii) the sum of two or more of the four major peptides, and/or (iii) the at least one related impurity.

The term "related impurity" refers to any compound which produces a peak on the HPLC chromatogram other than the peaks corresponding to the four major protamine peptides. Related impurities include, without limitation, degradation products of the four major peptides, peptides derived from a method of isolating protamine from a natural source, and peptides derived from a process of making protamine recombinantly. Related impurities also include non-peptide compounds detected by the HPLC method, such as nucleic acids and carbohydrates.

Preferably, the determination of the concentration of each of the four major peptides and each related impurity is by area under the peak of each major peptide or related impurity as a percentage of the total area under all peaks observed in the chromatogram.

In certain embodiments, the HPLC is performed using a C-18 chromatography column. In some embodiments, the HPLC column is an XBridge BEH300 C18 Peptide Separation Technology (PST) column which utilizes a wide-pore (300 Å) trifunctionally bonded ethylene bridged hybrid (BEH) particle (Waters Corporation, Milford, Mass.).

In some embodiments, the HPLC is performed at a column temperature of less than 55° C. For example, the HPLC can be performed at a column temperature of about 25° C., about 30° C., about 35° C., about 40° C., about 45° C., about 50° C., or any range therein. In certain embodiments, the HPLC is performed at a column temperature of about 40° C.

In certain embodiments, the HPLC is performed using a flow rate of less than 1.0 mL/minute. For example, the HPLC can be performed using a flow rate of about 0.9 mL/minute, about 0.8 mL/minute, about 0.7 mL/minute, about 0.6 mL/minute, about 0.5 mL/minute, or any range therein. In certain embodiments, the HPLC is performed using a flow rate of about 0.6 mL/minute.

In certain embodiments, the high pressure liquid chromatography is performed using a mobile phase A consisting of a monobasic sodium phosphate aqueous solution and a mobile phase B consisting of a mixture of a monobasic sodium phosphate aqueous solution and acetonitrile. In a preferred embodiment, the ratio of monobasic sodium phosphate aqueous solution to acetonitrile in the mobile phase B is about 65:35. In certain embodiments, the high pressure liquid chromatography is performed using a gradient consisting of variable amounts of mobile phase A and mobile phase B.

In any embodiment of the invention, a sample solution comprising protamine can be a solution of the sample of protamine in aqueous sodium chloride.

As will be readily understood by one of ordinary skill in the art, the solvent eluting from the terminus of a chromatography column is referred to as an eluent. The eluent can be monitored using any suitable detection method. A preferred detection method is determining the UV absorbance of at least a portion of the eluent as the chromatography is in process. In preferred embodiments, the chromatogram is determined by measuring a UV absorbance of the eluent at a wavelength of 214 nm.

In certain preferred embodiments, the peak of the at least one related impurity is present between the peaks corresponding to the major peptides corresponding to Peptides 2 and 3 in FIG. 1. In certain preferred embodiments, two peaks corresponding to at least two related impurities are present between the peaks corresponding to the major peptides corresponding to Peptides 2 and 3 in FIG. 1.

In certain embodiments, the determination about the sample of protamine comprises selecting a batch of protamine as a result of the determination.

As shown in the example chromatography and demonstrated in the data below comparing both the method of the present invention and a comparative method, the method of the present invention demonstrates superior resolution of major peptides from the related peptides around and between the major peptides resulting in a more accurate quantitation of the major peptides and more accurate results for the related peptides than the comparative method. Since the present method has better selectivity than the comparative method, it is easier to integrate all related peptides present, especially between major peptides 2 and 3.

In some embodiments, the method for analyzing a sample of protamine raw material results in a determination of the concentration of the sum of the four major peptides corresponding to Peptides 1-4 in FIG. 1 which is 85% w/w or more, e.g., 85.5% w/w or more, 86.0% w/w or more, 86.5% w/w or more, 87.0% w/w or more, 87.5% w/w or more, 88.0% w/w or more, 88.5% w/w or more, 89.0% w/w or more, 89.5% w/w or more, 90.0% w/w or more, 90.5% w/w or more, 91.0% w/w or more, 91.5% w/w or more, or 92.0% w/w or more. In other embodiments, the method for analyzing a sample of protamine raw material results in a determination of the concentration of the sum of the four major peptides corresponding to Peptides 1-4 in FIG. 1 which is 97.0% w/w or less, e.g., 96.5% w/w or less, 96.0% w/w or less, 95.5% w/w or less, 95.0% w/w or less, 94.5% w/w or less, 94.0% w/w or less, 93.5% w/w or less, 93.0% w/w or less, 92.5% w/w or less, 92.0% w/w or less, 91.5% w/w or less, 90.0% w/w or less, or 89.5% w/w or less. In yet other embodiments, the method for analyzing a sample of protamine raw material results in a determination of the concentration of the sum of the four major peptides corresponding to Peptides 1-4 in FIG. 1 which is in a range bounded by any of the foregoing values. For example, the method for analyzing a sample of protamine raw material can result in a determination of the concentration of the sum of the four major peptides corresponding to Peptides 1-4 in FIG. 1 which is 86.0%-95.0%, 87.5%-90.0% w/w, 88.0%-91.0% w/w, 88.5%-93.0% w/w, 90.0%-92.5% w/w, or 87.0%-90.5%.

In some embodiments, the method for analyzing a sample of protamine finished product, such as a pharmaceutical composition comprising protamine, results in a determination of the concentration of the sum of the four major peptides corresponding to Peptides 1-4 in FIG. 1 which is 76.0% w/w or more, e.g., 77.0% w/w or more, 77.5% w/w or more, 78.0% w/w or more, 78.5% w/w or more, 79.0% w/w or more, 79.5% w/w or more, 80.0% w/w or more, 80.5% w/w or more, 82.0% w/w or more, 83.5% w/w or more, 85.0% w/w or more, 86.5% w/w or more, 88.0% w/w or more, or 89.5% w/w or more. In other embodiments, the method for analyzing a sample of protamine finished product results in a determination of the concentration of the sum of the four major peptides corresponding to Peptides 1-4 in FIG. 1 which is 93.0% w/w or less, e.g., 92.5% w/w or less, 92.0% w/w or less, 91.5% w/w or less, 91.0% w/w or less, 90.5% w/w or less, 90.0% w/w or less, 89.0% w/w or less, 87.5% w/w or less, 86.0% w/w or less, 84.5% w/w or less, 83.0% w/w or less, 81.5% w/w or less, or 80.0% w/w or less. In yet other embodiments, the method for analyzing a sample of protamine finished product results in a determination of the concentration of the sum of the four major peptides corresponding to Peptides 1-4 in FIG. 1 which is in a range bounded by any of the foregoing values. For example, the method for analyzing a sample of protamine raw material can result in a determination of the concentration of the sum of the four major peptides corresponding to Peptides 1-4 in FIG. 1 which is 76.0%-92.5%, 77.5%-91.0% w/w, 78.0%-83.0% w/w, 79.0%-86.0% w/w, 80.5%-89.0% w/w, or 85.0%-91.0%.

The methods comprise chromatographically separating a sample comprising protamine using liquid chromatography. The invention is not limited to any particular manner of performing liquid chromatography. In general, the chromatographic separation step includes using at least one liquid chromatography (LC) column. In some embodiments, multiple LC columns are used, such as two or more, or three or more, or four or more LC columns. In some such embodiments two, three, four, five, six, eight, or ten LC columns are used. In some such embodiments, two or more of these LC columns are arranged parallel to each other.

The invention is not limited to any particular types of columns. Any column suitable for the separation of protamine can be used. In some embodiments, one or more analytical columns are used. In some such embodiments, one or more reverse phase columns are used. In some embodiments, the method employs two or more reverse phase columns in parallel.

Further, the invention is not limited to any particular mobile phase. Any suitable mobile phase or phases can be used, as long as the mobile phase or phases are suitable for use with a particular LC column and for chromatographically separating the protamine sulfate in the LC column. In some embodiments, the mobile phase or phases are a polar solvent system or systems. The polar solvent system or systems can include one or more polar solvents, including but not limited to water, methanol, acetonitrile, or a mixture of two or more of the foregoing. The polar solvent system can include one or more aqueous buffer solutions. For example, the polar solvent system can comprise, consist essentially of, or consist of an aqueous solution of one of more buffers. In other embodiments, the aqueous solution of one or more buffers further includes one or more polar solvents in addition to water. In some embodiments, the mobile phase employs a gradient obtained by mixing two or more solvents, such that the relative ratios of the two or more solvents are varied over time.

As noted above, two or more LC columns (e.g., reverse phase columns) can be used in parallel, e.g., to improve throughput. In some such embodiments, a protamine sulfate sample e.g., a partially purified sample or a crude mixture) is introduced to the two or more LC columns at different times. In some embodiments, the introduction of the test sample to the two or more LC columns is staggered, meaning that there is a pre-determined time interval separating the introduction of sample to two or more LC columns. Appropriate time intervals can be selected based on various factors, including the elution time, column chemistries, and the potential need to avoid interfering with the analysis of the protamine sulfate eluted from one or more of the other LC columns.

In some embodiments of the invention, another LC column can be placed in series with another column. For example, in some embodiments, suitable guard columns can be employed. Those of skill in the art are able to select appropriate guard columns for use in the present methods. In some embodiments, a guard column is placed in parallel with another LC column, and both the guard column and the LC column are reverse phase columns. Such series of two or more columns can also be arranged in parallel, such that there are two or more series of columns operating in parallel, where each series contains two or more columns.

The following examples further illustrate the invention but, of course, should not be construed as in any way limiting its scope.

Example 1

This example demonstrates the use of high performance liquid chromatographic (HPLC) analysis for the determination of nucleotidic impurities in Protamine Sulfate, USP raw material by HPLC.

Summaries of the analytical solutions and HPLC parameters used to analyze samples for the presence or amount of at least one nucleotidic component are provided in the following tables.

Analytical Solutions

| | |
|---|---|
| Mobile Phase A (MP A) | 20 mM ammonium acetate pH 4.1 |
| Mobile Phase B (MP B) | Acetonitrile (ACN) |
| Standard Solution | The Standard Solution contains approximately 0.125 μg/mL of USP Adenosine Reference Standard (RS) in water. |
| System Sensitivity Solution | The System Sensitivity Solution contains approximately 0.05 μg/mL of Adenosine RS in water. |
| Nucleoside Identification Solution | The Nucleoside Identification Solution contains approximately 2.5 μg/mL uridine, guanosine, cytidine, thymidine, 2'-deoxyadenosine, 2'-deoxyguanosine, 2'-deoxycytidine, and 5-methyl-2'-deoxycytidine in water. |
| Reaction Buffer | 20 mM magnesium chloride (MgCl2), 20 mM Tris, 100 mM sodium chloride (NaCl) in water pH 7.9 |
| Phosphodiesterase I (PDE I) Solution: | 0.1 U/μL in 1:1 Reaction Buffer: Glycerol |
| Enzyme Digest Solution | 50 U/mL Benzonase Endonuclease, 44.4 U/mL Alkaline Phosphatase, and 2.5 U/mL PDE I in Reaction Buffer |
| Diluent | 64 mM Sodium Bicarbonate pH 8.5 |
| Sample Solution | The Sample Solution contains approximately 0.5 mg/mL protamine sulfate. |
| Positive Control Sample Solution | The Positive Control Sample Solution contains approximately 0.5 mg/mL protamine sulfate and 0.5 μg/mL of DNA. |

HPLC Parameters

| | | | |
|---|---|---|---|
| Column | Phenomenex Synergi Fusion-RP 80 Å, 4.6 × 150 mm, 4 μm, Part Number 00F-4424-E0 | | |
| Column Temperature | 25 ± 3° C. | | |
| Flow Rate | 0.9 mL/min | | |
| Autosampler Temperature | 37 ± 2° C. | | |
| Injection Volume | 100 μL | | |
| Detector | UV at 260 nm | | |
| Run Time | About 30 minutes | | |
| | Time, min | % MPA | % MPB |
| Gradient Profile | 0 | 98 | 2 |
| | 5 | 98 | 2 |
| | 15 | 80 | 20 |
| | 20 | 80 | 20 |
| | 20.1 | 98 | 2 |
| | 30 | 98 | 2 |
| System Suitability | 1. The signal-to-noise ratio (S/N) of the Adenosine peak in the System Sensitivity Solution is NLT 10. 2. The percent relative standard deviation (% RSD) of the Adenosine peak area responses in six (6) replicate injections of Reference Solution is not more than (NMT) 10%. 3. The resolution between 2'-deoxycytidine and the uridine peak in the Nucleoside Identification Solution is NLT 1.5. 4. All four nucleoside peaks for DNA: 2'-deoxyadenosine; 2'-deoxyguanosine; 2'-deoxycytidine; and thymidine, must be present in Positive Control Sample Solution. | | |

Figure 2:
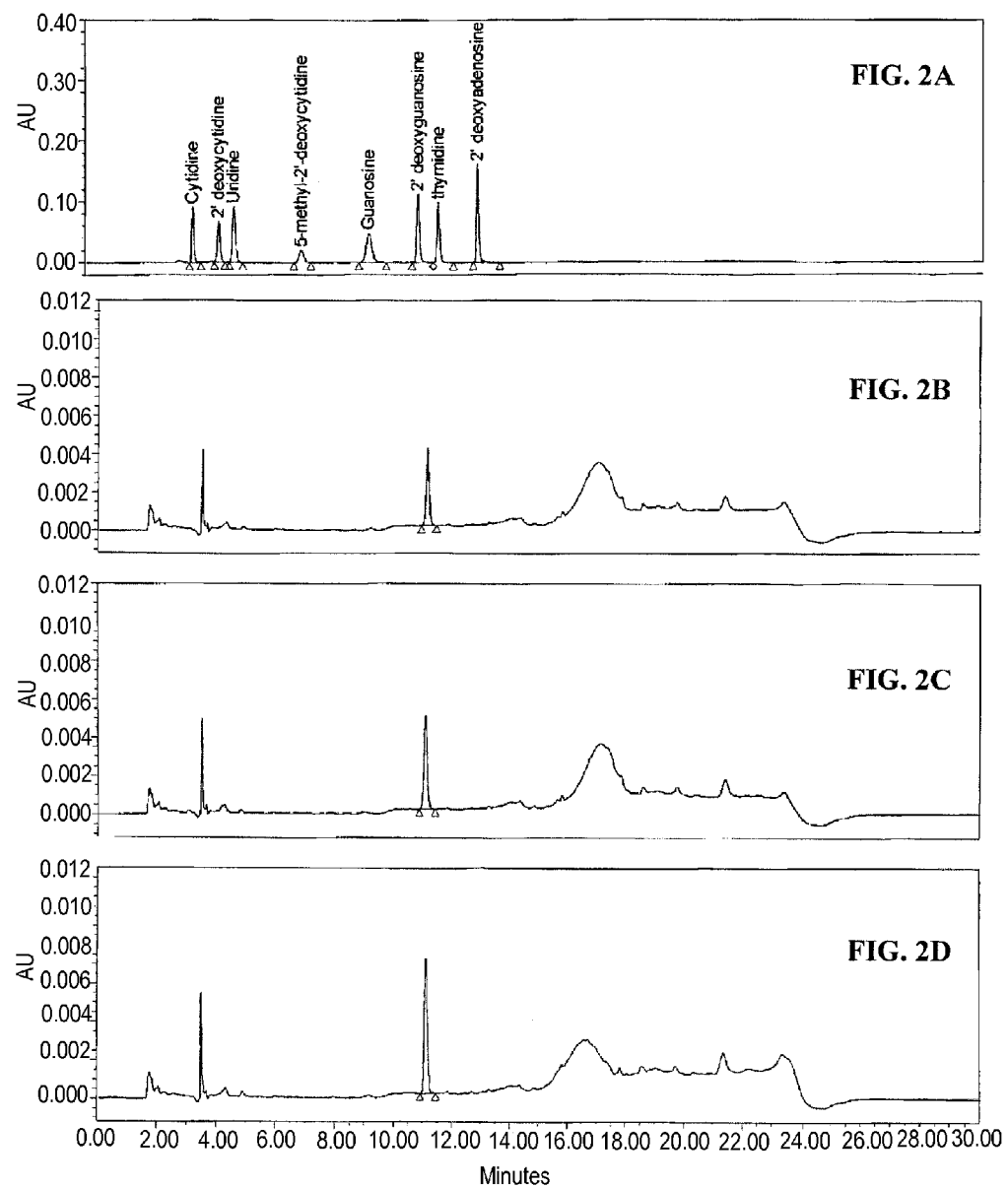

The results of the analysis of the Nucleoside Identification Solution and Protamine Sulfate, USP Raw Material obtained from three different sources are shown in FIG. 2.

The results of this example demonstrate a method for analyzing a sample for the presence or amount of at least one nucleotidic component by HPLC.

Example 2

This example demonstrates a method for analyzing a protamine sample for the presence or amount of at least one nucleotidic impurity according to an embodiment of the invention.

Equipment
1. HPLC system equipped with a temperature controlled column compartment, a heated autosampler, a single wavelength UV detector, sample heater, and a suitable data acquisition system
2. HPLC column: Phenomenex Synergi Fusion-RP 80 Å, 4.6×150 mm, 4 μm, Part Number 00F-4424-E0
3. HPLC Guard Column: Phenomenex Security Guard Cartridge Kit, Part Number KJ0-4282
4. HPLC Guard Cartridge: Phenomenex Security Guard Cartridge Fusion-RP 4 X 3.0 mm ID Part Number AJ0-7557
5. 3004 HPLC vial, Agilent Part #5188-6591, or equivalent
6. Blue Screw Caps for HPLC vial, Agilent Part #5182-0717, or equivalent
7. 1000 μL Eppendorf vial, Fisher Part#02-681-284 or equivalent
8. Calibrated analytical balance
9. Calibrated pH meter
10. Calibrated micropipettes
11. Heat block capable of maintaining 100±3° C.
12. Calibrated Thermometer
13. Oven capable of maintaining 37° C.±3° C.
14. Mini Centrifuge, Fisher Scientific, Cat #05-090-100, or equivalent
15. Nutating Mixer, Fisher Scientific, Cat #05-450-213, or equivalent
16. Calibrated Timers
17. Sonicator
18. Freezer (−15 to −25° C.)
19. Refrigerator (2 to 8° C.)
20. Class A volumetric glassware
21. Other standard laboratory glassware and equipment Materials
1. Acetonitrile, HPLC grade (ACN)
2. Water, HPLC grade or Purified Water, USP
3. Ammonium Acetate, ACS grade, or equivalent
4. Glacial Acetic Acid, ACS grade, or equivalent
5. Magnesium Chloride 6-Hydrate, USP grade, or equivalent
6. Tris(hydroxymethyl)amino methane, ACS grade (tris), or equivalent
7. Sodium Chloride, ACS grade, or equivalent
8. 1N Hydrochloric Acid, NIST grade
9. 1N Sodium Hydroxide, NIST grade
10. Glycerol, ACS grade, or equivalent
11. Benzonase, 99%, 25 U/μL EMD Part #70664-3
12. Phosphodiesterase I 100 U/vial, Worthington Biochemical Part # LS003926 (PDE I)
13. Alkaline Phosphatase, Sigma Part # P7923-10kU (AP)
14. Protamine Sulfate, USP raw material
15. USP Adenosine Reference Standard (RS), Catalog #1012123
16. Uridine Reference Standard (RS), (Sigma Product # U6381), or equivalent
17. Guanosine RS, (Acros Product #41113), or equivalent
18. Cytidine RS, (Acros Product #11181), or equivalent
19. Thymidine RS, (Acros Product #22674), or equivalent 20. 2'-Deoxyadenosine Hydrate RS, (Acros Product #15499), or equivalent
21. 2'-Deoxyguanosine Hydrate RS, (Acros Product #22673), or equivalent
22. 2'-Deoxycytidine RS, (Sigma Product # D3897), or equivalent
23. 5-Methyl-2'-Deoxycytidine RS, (Berry Product # PY 7635), or equivalent
24. Deoxyribonucleic acid sodium salt (DNA) from calf thymus, (Sigma Product # D1501)
25. Trypsin from porcine pancreas, (Sigma Product # T6567)

Preparations
Mobile Phase a (20 mM Ammonium Acetate pH 4.1)
Accurately weigh and transfer about 3.08 g ammonium acetate in a 2-L flask, add 2000 mL water, and mix until dissolved. Adjust pH to 4.1±0.1 with glacial acetic acid. Degas for about 2 minutes under vacuum with sonication. Prepare a proportionally larger quantity if necessary.

Mobile Phase B (100% Acn)
Transfer 2000 mL ACN into a 2-L flask. Degas for about 1 minute under vacuum with sonication.

Nucleoside Identification Solution
Accurately weigh and transfer about 25 mg of Uridine RS, Guanosine RS, Cytidine RS, Thymidine RS, 2'-Deoxyadenosine RS, 2'-Deoxyguanosine RS, 2'-Deoxycytidine RS, and 5-Methyl-2'-Deoxycytidine RS into a 200 mL volumetric flask, add approximately 185 mL of water, dissolve with sonication and vortexing (if necessary), dilute to volume, and mix. Transfer 2.0 mL of this solution into a 100-mL volumetric flask, dilute to volume with water, and mix. This solution contains approximately 2.5 μg/mL of each nucleoside.

Adenosine Stock Standard Solution
Accurately weigh and transfer about 25 mg of USP Adenosine RS into a 100-mL volumetric flask, add approximately 85 mL of water, and dissolve with sonication and vortexing (if necessary). Dilute to volume with water and mix. Transfer 10.0 mL of this solution into a 100-mL volumetric flask, dilute to volume with water and mix. This solution contains approximately 25 μg/mL adenosine.

Standard Solution
Transfer 1.0 mL of Adenosine Stock Standard Solution into a 200-mL volumetric flask, dilute to volume with water, and mix. This solution contains approximately 0.125 μg/mL of adenosine.

System Sensitivity Solution
Transfer 4.0 mL Standard Solution into a 10-mL volumetric flask, dilute to volume with water, and mix. This solution contains approximately 0.05 μg/mL adenosine.

Reaction Buffer
Accurately weigh and transfer 410 mg magnesium chloride hexahydrate, 240 mg tris, and 580 mg sodium chloride into a 100-mL volumetric flask, dissolve in 75 mL water, and mix. Adjust pH to 7.9±0.1 with 1N hydrochloric acid. Dilute to volume with water and mix. Store refrigerated at 5±3° C.

PDE I Diluent (1:1 Reaction Buffer:Glycerol)
Transfer 5.0 mL glycerol and 5.0 mL Reaction Buffer into a 20-mL volumetric flask and vortex to mix.

PDE I Solution
Using a small spatula carefully transfer the contents of 1 vial Phosphodiesterase I (PDE I) into a 1000 μL Eppendorf vial and reconstitute with 1000 μL PDE I Diluent. This solution has a concentration of approximately 0.1 U/μL.

Enzyme Digest Solution
Add 10 μL Benzonase, 222 U Alkaline Phosphatase (AP), and 125 μL PDE I Solution to 5.0 mL Reaction Buffer. This solution can be proportionally adjusted to prepare the desired amount. This solution contains 50 U/mL Benzonase, 44.4 U/mL AP, and 2.5 U/mL PDE I. Calculate the volume of AP to be used as follows using the C of A per Equation 1:

$$\mu LAP = \frac{\text{Units } AP}{(\text{Units/mg Protein}) \times (\text{mg Protein/mL})} \times \frac{1000 \mu L}{mL} \quad (1)$$

where,
Units AP=Units of AP needed to prepare Enzyme Digest Solution
Units/mg Protein=Enzymatic activity of AP from C of A in Units/mg Protein
mg Protein/mL=Protein by Biuret with TCA Precipitation from C of A in mg protein/mL Diluent (64 mM Sodium Bicarbonate pH 8.5)
Accurately weigh and transfer 2.70 g sodium bicarbonate into a 500-mL volumetric flask, dissolve in 450 mL water, and mix. Adjust pH to 8.5±0.1 with 1N hydrochloric acid or 1N sodium hydroxide. Dilute to volume with water and mix. Store refrigerated at 5±3° C.

1 mM Hydrochloric (HCl) Acid
Transfer 1.0 mL 0.1N hydrochloric acid into a 100-mL volumetric flask, dilute to volume with water and mix.

Blank Solution
Listed below are the steps necessary to prepare Blank Solution.
1. Reconstitute 20 μg vial of trypsin with 20 μL 1 mM HCl. Transfer 100 μL of the Diluent into a trypsin reagent vial. Digest for not less than (NLT) 60 minutes in vial with mixing at 37±2° C. using an oven.
2. Using a heat block inactivate trypsin for NLT 30 minutes at 100±3° C. Flash cool at −20° C. for 2-3 minutes. Spin reagent vial in mini centrifuge for approximately 30 seconds. Confirm that sample solution accumulates at the bottom of the reagent vial.
3. Transfer entire reaction mixture (120 μL) into a 300 μL HPLC vial, add 80 μL Enzyme Digest Solution and mix with the micropipette. Incubate NLT 60 minutes in the autosampler at 37° C. before injection.

Sample Solution
Listed below are the steps necessary to prepare Sample Solution.
1. Accurately weigh and transfer about 20 mg Protamine Sulfate, USP raw material into a 20-mL volumetric flask, dilute to volume with Diluent, and mix.
2. Reconstitute 20 μg vial of trypsin with 20 μL 1 mM HCl. Transfer 100 μL of the 1 mg/mL Protamine Sulfate solution into a trypsin reagent vial. Digest for NLT 60 minutes in vial with mixing at 37±2° C. using an oven.
Using a heat block inactivate trypsin for NLT 30 minutes at 100±3° C. Flash cool at −20° C. for 2-3 minutes. Spin reagent vial in mini centrifuge for approximately 30 seconds. Confirm that sample solution accumulates at the bottom of the reagent vial.
4. Transfer entire reaction mixture (120 μL) into a 300-4 HPLC vial, add 80 μL Enzyme Digest Solution and mix with the micropipette. Incubate NLT 60 minutes in the autosampler at 37° C. before injection. This solution contains approximately 0.5 mg/mL protamine sulfate.

Positive Control Sample Solution (0.1% DNA)
Listed below are the steps necessary to prepare Sample Solution.
1. Accurately weigh and transfer about 20 mg Protamine Sulfate, USP raw material into a 20-mL volumetric flask, dilute to volume with Diluent, and mix.
2. Accurately weigh and transfer about 1.1 mg of DNA into a 100 mL volumetric flask, dilute to volume with water, and mix to dissolve.
Correct for purity [from Certificate of Analysis (COA)] of the DNA while weighing. % Purity=A260 Unit/mg solid absorbance value (from COA÷20)
Note: Do not sonicate or vortex DNA to dissolve.
3. Reconstitute 20 µg vial of trypsin with 20 µL 1 mM HCl. Transfer 90 µL of the 1 mg/mL Protamine Sulfate solution and 10 µL of the 10 µg/mL DNA solution into a trypsin reagent vial. Digest for NLT 60 minutes in vial with mixing at 37±1° C. using an oven/chamber.
4. Using a heat block inactivate trypsin for NLT 30 minutes at 100±3° C. Flash cool at −20° C. for 2-3 minutes. Spin reagent vial in mini centrifuge for approximately 30 seconds. Confirm that sample solution accumulates at the bottom of the reagent vial.
5. Transfer entire reaction mixture (120 µL) into a 300-µL HPLC vial, add 80 µL Enzyme Digest Solution and mix with the micropipette. Incubate NLT 60 minutes in the autosampler at 37° C. before injection. This solution contains approximately 0.5 mg/mL protamine sulfate.

DNA Control Sample Solution (0.1% DNA)
Listed below are the steps necessary to prepare Sample Solution.
1. Accurately weigh and transfer about 1.1 mg of DNA into a 100 mL volumetric flask, dilute to volume with water, and mix to dissolve.
Correct for purity (from COA) of the DNA while weighing. % Purity=A260 Unit/mg solid absorbance value (from COA÷20)
Note: Do not sonicate or vortex DNA to dissolve.
2. Reconstitute 20 µg vial of trypsin with 20 µL 1 mM HCl. Transfer 90 µL of Diluent and 10 µL of the 10 µg/mL DNA solution into a trypsin reagent vial. Digest for NLT 60 minutes in vial with mixing at 37±1° C. using an oven/chamber.
3. Using a heat block inactivate trypsin for NLT 30 minutes at 100±3° C. Flash cool at −20° C. for 2-3 minutes. Spin reagent vial in mini centrifuge for approximately 30 seconds. Confirm that sample solution accumulates at the bottom of the reagent vial.
4. Transfer entire reaction mixture (120 µL) into a 300-4 HPLC vial, add 80 µL Enzyme Digest Solution and mix with the micropipette. Incubate NLT 60 minutes in the autosampler at 37° C. before injection. This solution contains approximately 0.5 mg/mL protamine sulfate.

Chromatographic System
HPLC Parameters
Column: Phenomenex Synergi Fusion-RP 80 Å, 4.6×150 mm, 4 µm, Part Number 00F-4424-E0
Guard Column: Phenomenex Security Guard Cartridge Kit, Part Number KJ0-4282 Phenomenex Security Guard Cartridge, Synergi Fusion-RP 4×3.0 mm, Part Number AJ0-7557
Column Temperature: 25±3° C.
Mobile Phase A (MP A): 20 mM ammonium acetate pH 4.1
Mobile Phase B (MP B): Acetonitrile Gradient:

| Time  | % MPA | % MPB |
|-------|-------|-------|
| 0     | 98    | 2     |
| 5.00  | 98    | 2     |
| 15.00 | 80    | 20    |
| 20.00 | 80    | 20    |
| 20.10 | 98    | 2     |
| 30.00 | 98    | 2     |

Flow Rate: 0.9 mL/min.
Injection Volume: 100 µL
Detector: 260 nm
Needle Wash: Water
Autosampler Temperature: 37±1° C.
Run Time: 30 minutes
Robustness Range

| Parameter | Range | Change |
|---|---|---|
| Column Temperature | 20-30° C. | ±5° C. |
| Mobile Phase A pH | 4.0-4.2 | ±0.1 pH |
| Diluent pH | 8.4-8.6 | ±0.1 pH |
| Digest Time (minutes) | 45-75 | ±15 |
| Reaction Buffer pH | 7.8-8.0 | ±0.1 pH |
| Inactivation Time (minutes) | 20-40 | ±10 |
| Incubation Temperature | 36-38° C. | ±1° C. |

System Suitability
1. Inject six (6) replicates of the Standard Solution and record the chromatograms. The percent relative standard deviation (% RSD) of the areas of the adenosine peak is not more than (NMT) 10%.
2. The resolution between the 2'-deoxycytidine peak and the Uridine peak is NLT 1.5 for the injection of the Nucleoside Identification Solution.
3. The signal-to-noise ratio (S/N) of the adenosine peak in the System Sensitivity Solution is NLT 10.
4. All four nucleoside peaks for DNA-2' deoxycytidine, 2' deoxyguanosine, Thymidine, 2' deoxyadenosine must be present in the Positive Control Sample Preparation.

Procedure
Separately inject 100 µL of the water, Blank Solution, System Sensitivity Solution, Nucleoside Identification Solution, Standard Solution, Sample Solution, and Positive Control Sample Preparation and record the chromatograms.

Nucleotidic Impurity Calculations
Area Reject Value (Q)
Calculate the area reject value, Q, which corresponds to a S/N of 10. The Q value is calculated using Equation (2) and will be used as the cut-off area for considering individual peaks.

$$Q = (10 \times A_{sss})/S/N \tag{2}$$

where:
$A_{sss}$=Peak area of adenosine in the System Sensitivity Solution
S/N=Signal-to-noise ratio of the adenosine peak in the System Sensitivity Solution Standard Solution
Calculate the concentration of adenosine, in mg/mL, using Equation (3).

$$C_{std} = W_{std}/DF \tag{3}$$

where:
$C_{std}$=Concentration of adenosine in the Standard Solution, in mg/mL
$W_{std}$=Weight of USP Adenosine RS, in mg
DF=200,000 mL (Dilution Factor)

Nucleotidic Impurities

Calculate the % Nucleotidic Impurities using Equation (4):

$$\% \text{ NUCLEOTIDIC IMP.} = \sum \left( \frac{C_{STD}}{A_{STD}} \times A_i \times \frac{MW_{RATIO}}{RRF_1} \right) \times \frac{DF}{W_{SAMPLE}} \times 100\% \quad (4)$$

where:
- $C_{std}$=Concentration of adenosine in the Standard Solution, in mg/mL
- $A_{std}$=Average peak area (n=6) of adenosine in the Standard Solution
- $A_i$=Peak area of each impurity above Q in the Sample Solution
- $RRF_i$=For known impurities see Table I otherwise use 1.00
- $MW_{ratio}$=For known impurities see Table I otherwise use 1.00
- DF=40 mL (Dilution Factor)
- $W_{sample}$=Sample weight of Protamine Sulfate, USP, in mg Relative Retention Times (RT), Relative Response Factors (RRF), and Molecular Weight (MW) Ratios for Known Impurities

| Nucleoside | RRT (min) | RRF | $MW_{ratio}$ |
|---|---|---|---|
| Cytidine | 0.28 | 0.53 | 1.2548 |
| 2'-Deoxycytidine | 0.35 | 0.56 | 1.2727 |
| Uridine | 0.39 | 0.75 | 1.2537 |
| 5-Methyl-2'-Deoxycytidine HCl | 0.55 | 0.25 | 1.2569 |
| Guanosine | 0.72 | 0.74 | 1.2188 |
| 2'-Deoxyguanosine | 0.87 | 0.83 | 1.2319 |
| Thymidine | 0.93 | 0.68 | 1.2558 |
| Adenosine | 1.00 | 1.00 | 1.2319 |
| 2'-Deoxyadenosine | 1.04 | 1.09 | 1.2466 |

This example demonstrates a method of analyzing a protamine sample for the presence or amount of at least one nucleotidic impurity according to an embodiment of the invention.

Example 3

This example demonstrates a method for analyzing a sample of protamine sulfate comprising four major peptides and related impurities by an HPLC method.

Equipment
1. An HPLC system (Agilent 1100 or 1200, or Dionex Ultimate 3000) equipped with a temperature controlled column compartment, temperature controlled autosampler, variable wavelength UV/VIS detector, and a suitable data acquisition system
2. HPLC column: Waters Xbridge BEH 300, C-18 (3.5 µm, 4.6 mm×150 mm) P/No 186003613
3. For Agilent 1100 or 1200 only, Thermal Column Heat Block, P/No G1316-60001
4. Analytical balance, calibrated
5. pH meter, calibrated
6. Vortex mixer
7. Sonicator
8. Hygrometer, calibrated
9. Class A volumetric glassware
10. Other standard laboratory glassware and equipment Materials
1. Acetonitrile, HPLC grade
2. Purified Water, USP or HPLC grade, or equivalent
3. Sodium phosphate monobasic monohydrate, HPLC grade, or equivalent
4. Hydrochloric acid, ACS grade
5. Sodium chloride, ACS grade
6. Protamine Sulfate, USP Raw Material
7. Protamine Sulfate Injection, USP Finished Product
8. Nitrogen gas, Ultra High Purity Grade Preparations Mobile Phase A Accurately weigh and transfer about 22.1 grams of sodium phosphate monobasic monohydrate into a 2 L container containing 2 L of water and mix. Adjust pH to about 1.9±0.2 with hydrochloric acid. Degas under vacuum with sonication for about 5 minutes. Prepare proportionately larger quantities as needed.

Mobile Phase B

Transfer 650 mL of Mobile Phase A and 350 mL of acetonitrile into a suitable container and mix. Degas under vacuum with sonication for about 3 minutes. Prepare proportionately larger quantities as needed.

Diluent

Accurately weigh and transfer about 9 grams of sodium chloride into a 1-L suitable container. Transfer 1000 mL of water into the container and mix. Prepare proportionately larger quantities as needed.

Reference Solution

Accurately weigh and transfer about 100 mg of Protamine Sulfate, USP raw material into a 10-mL volumetric flask, dissolve and dilute to volume with Diluent with alternating vortexing and sonication. The Reference Solution contains approximately 10 mg/mL of protamine sulfate. Note: weigh protamine sulfate raw material under nitrogen with less than 20% relative humidity.

System Sensitivity Solution

Pipette 5.0 mL of the Reference Solution into a 25-mL volumetric flask, dilute to volume with Diluent, and mix. Pipette 3.0 mL of this solution into a 100-mL volumetric flask, dilute to volume with Diluent, and mix. The System Sensitivity Solution contains approximately 60 µg/mL of protamine sulfate.

Raw Material Sample Solution

Accurately weigh and transfer about 100 mg of Protamine Sulfate, USP raw material into a 10-mL volumetric flask, dissolve and dilute to volume with Diluent with alternating vortexing and sonicating. The Raw Material Sample Solution contains approximately 10 mg/mL of protamine sulfate. Note: weigh protamine sulfate raw material under nitrogen with less than 20% relative humidity.

Finished Product Sample Solution

The Finished Product Sample Solution has a concentration of approximately 10 mg/mL protamine sulfate. Transfer appropriate aliquot of finished product sample into a HPLC vial and inject sample neat.

Chromatographic System

HPLC Parameters

Mobile Phase A (MP A): 80 mM sodium phosphate monobasic in water, pH 1.9±0.2

Mobile Phase B (MP B): 80 mM sodium phosphate monobasic pH 1.9±0.2 in water:acetonitrile (65:35)

Gradient:

| Time (min) | MP A | MP B |
|---|---|---|
| 0.0 | 96.1 | 3.9 |
| 30.0 | 91.5 | 8.5 |
| 40.0 | 91.5 | 8.5 |
| 41.0 | 1.0 | 99.0 |
| 51.0 | 1.0 | 99.0 |
| 52.0 | 96.1 | 3.9 |
| 70.0 | 96.1 | 3.9 |

Column: Waters XBridge BEH 300, C-18, 3.5 μm, 4.6 mm×150 mm, P/No 186003613
Column Temperature: 40−1+2° C.
Flow Rate: 0.6 mL/min.
Injection Volume: 10 μL
Autosampler Temperature: 25±3° C.
Detection: UV at 214 nm
Run Time: 70 minutes
Needle Wash: Acetonitrile:Water 50:50
Separation Mode: Gradient
   Robustness Conditions

| Condition | Range | Change |
|---|---|---|
| Column Temperature (40° C.) | 39 to 42° C. | −1 + 2° C. |
| Mobile Phase A pH (1.9) | 1.7 to 2.1 | ±0.2 |
| Mobile Phase A Buffer Concentration (80 mM) | 75 to 85 mM | ±5 mM |

System Suitability
Adjust sequence to inject the Reference Solution before the System Sensitivity Solution.
1. Chromatograph the System Sensitivity Solution. The signal-to-noise ratio (S/N) of the protamine sulfate peptide #2 peak is not less than (NLT) 10.
2. Chromatograph the Reference Solution. The percent relative standard deviation (% RSD) of the protamine sulfate peak area sum of four major peptide peak responses in five (5) replicate injections is not more than (NMT) 2.0%.
3. In the first Reference Solution injection, the resolution between peaks of peptide 1 and peptide 2 is not less than (NLT) 2.5. The resolution between peaks of peptide #2 and peptide #3 is NLT 1.8. The resolution between peaks of peptide #3 and peptide #4 is not less than NLT 2.5.
4. In the first Reference Solution injection, the column efficiency is NLT 4,000 theoretical plates for peptide #1, NLT 1,500 theoretical plates for peptide #2, NLT 3,500 theoretical plates for peptide #3, and NLT 4,500 theoretical plates for peptide #4.
   Procedure
   Separately inject 10 μL of Diluent, Reference Solution, System Sensitivity Solution, and Raw Material Sample Solution and/or Finished Product Sample Solution into the HPLC and record the chromatograms.
   Identification
   HPLC Retention Times
   The chromatogram of the Raw Material Sample Solution or Finished Product Sample Solution exhibits four (4) major peptide peaks for protamine sulfate, the retention time of which corresponds to that exhibited by protamine sulfate in the chromatogram of Reference Solution and meets the following criterion:

$$0.95 \leq (R_u/R_s) \leq 1.05 \quad (1)$$

where,
$R_u$=Retention time of each major peptide peaks 1-4 in the Raw Material Sample Solution or Finished Product Sample Solution
$R_s$=Retention time of each major peptide peaks 1-4 in the Reference Solution This example demonstrates a method of analyzing a protamine sample comprising four peptides and at least one impurity according to an embodiment of the invention.

Example 4

This example demonstrates a method for analyzing a sample of protamine sulfate comprising four major peptides corresponding to Peptides 1-4 in FIG. 1 and related impurities by the inventive method and a comparative method.

Method Summary for an Embodiment of the Inventive Method: The summaries of the HPLC preparations and parameters for an embodiment of the method of the invention are provided in Tables I and II.

TABLE I

| Preparations for an Embodiment of the Inventive Method | |
|---|---|
| Mobile Phase A (MP A) | 80 mM sodium phosphate monobasic monohydrate, pH 1.9 ± 0.2 (Buffer) |
| Mobile Phase B (MP B) | 65:35 Buffer:acetonitrile |
| Diluent | 0.9% sodium chloride in water |
| Reference Solution | The Reference Solution contains approximately 10 mg/mL of protamine sulfate raw material in Diluent. |
| System Sensitivity Solution | The System Sensitivity Solution contains approximately 60 μg/mL of Protamine Sulfate Reference Solution (0.2% of abundance of Peptide # 2 at 32%) in Diluent. |
| Raw Material (RM) Sample Solutions | Raw Material Sample Solution contains approximately 10 mg/mL protamine sulfate in Diluent. |
| Finished Product (FP) Sample Solutions | Finished Product Sample Solution contains approximately 10 mg/mL protamine sulfate (neat injection). |

TABLE II

| HPLC Parameters for an Embodiment of the Inventive Method | | | |
|---|---|---|---|
| Column | Waters X-Bridge BEH 300 C-18, 3.5 μm, 4.6 mm × 150 mm, P/No 186003613 | | |
| Column Temperature | 40° C. (−1° C. + 2.0° C.) | | |
| Flow Rate | 0.6 mL/min. | | |
| Autosampler Temperature | 25 ± 3° C. | | |
| Injection Volume | 10 μL | | |
| Detector | UV at 214 nm | | |
| Run Time | About 70 minutes | | |
| | Time (minutes) | % MP A | % MP B |
| Gradient Profile | 0 | 96.1 | 3.9 |
| | 30 | 91.5 | 8.5 |
| | 40 | 91.5 | 8.5 |
| | 41 | 1.0 | 99.0 |
| | 51 | 1.0 | 99.0 |
| | 52 | 96.1 | 3.9 |
| | 70 | 96.1 | 3.9 |

Method Summary for the Comparative Method: The summaries of the preparations and HPLC parameters for the comparative method are provided in Tables III and IV.

TABLE III

Preparations for Comparative Method

| | |
|---|---|
| Mobile Phase A (MP A) | 300 mM sodium phosphate, pH 1.8 (Buffer) |
| Mobile Phase B (MP B) | 93.5:6.5 Buffer:acetonitrile |
| Diluent | 0.01M HCl in water |
| Standard Solution | The Standard Solution contains approximately 0.5 mg/mL of protamine sulfate raw material in Diluent. |
| System Sensitivity Solution | Not Applicable |
| Raw Material (RM) Sample Solutions | Raw Material Sample Solution contains approximately 0.5 mg/mL protamine sulfate in Diluent. |
| Finished Product (FP) Sample Solutions | Finished Product Sample Solution contains approximately 0.5 mg/mL protamine sulfate. |

TABLE IV

HPLC Parameters for Comparative Method

| | |
|---|---|
| Column | Phenomonex Jupiter C-18, 5.0 μm, 4.6 mm × 250 mm, P/No OOG-4053-EO |
| Column Temperature | 55° C. |
| Flow Rate | 1.0 mL/min. |
| Autosampler Temperature | 25 ± 3° C. |
| Injection Volume | 100 μL |
| Detector | UV at 214 nm |
| Run Time | About 45 minutes |

| | Time (minutes) | % MP A | % MP B |
|---|---|---|---|
| Gradient Profile[1] | 0 | 85 | 15 |
| | 15 | 55 | 45 |
| | 25 | 55 | 45 |
| | 30 | 85 | 15 |
| | 45 | 85 | 15 |

[1]Note: Gradient profile was modified to address problems with late eluting peaks that were carrying over into the next sample injection. Therefore, run time was extended to equilibrate the column back to the initial conditions.

The percent total major peptide for raw material analyzed per the inventive method ranged from 88.84 to 94.47 and per the comparative method ranged from 90.26 to 95.82. The largest related peptide for raw material analyzed in the inventive method was 3.2% and in the comparative method was 2.3%. The percent total related peptide for raw material analyzed per the inventive method ranged from 5.4 to 12.3 and per the comparative method ranged from 4.1 to 9.7.

The percent total major peptide for finished product analyzed per the inventive method ranged from 77.35 to 91.07 and per the comparative method ranged from 80.06 to 92.12. The largest related peptide for finished product analyzed per the inventive method was 3.61% and per the comparative method was 5.67%. The percent total related peptide for finished product analyzed per the inventive method ranged from 8.9 to 22.5 and per the comparative method ranged from 7.8 to 19.9.

Figure 3:
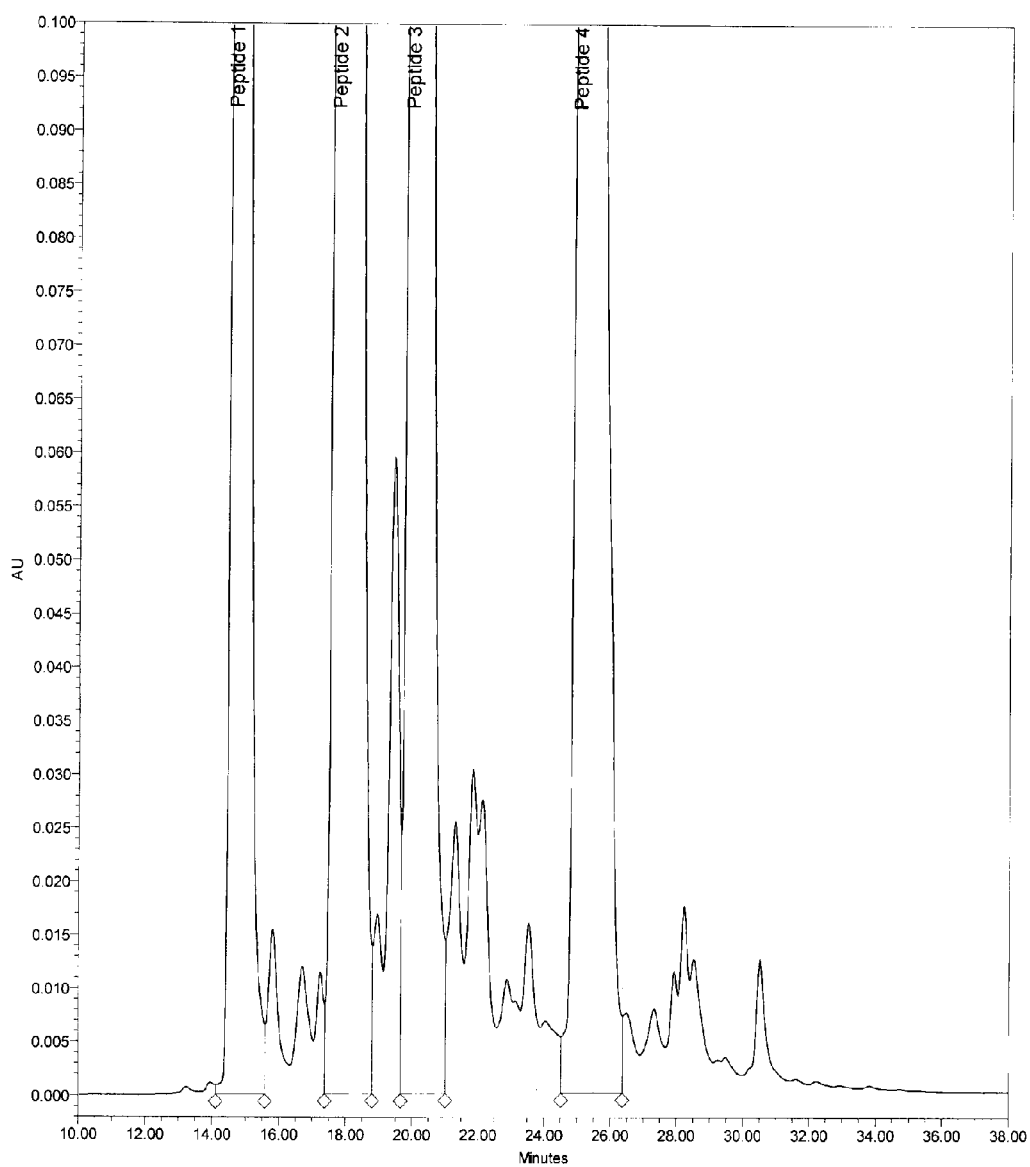
FIG. 3 depicts an expanded scale high pressure liquid chromatogram of the chromatogram depicted in FIG. 1.
Figure 4:
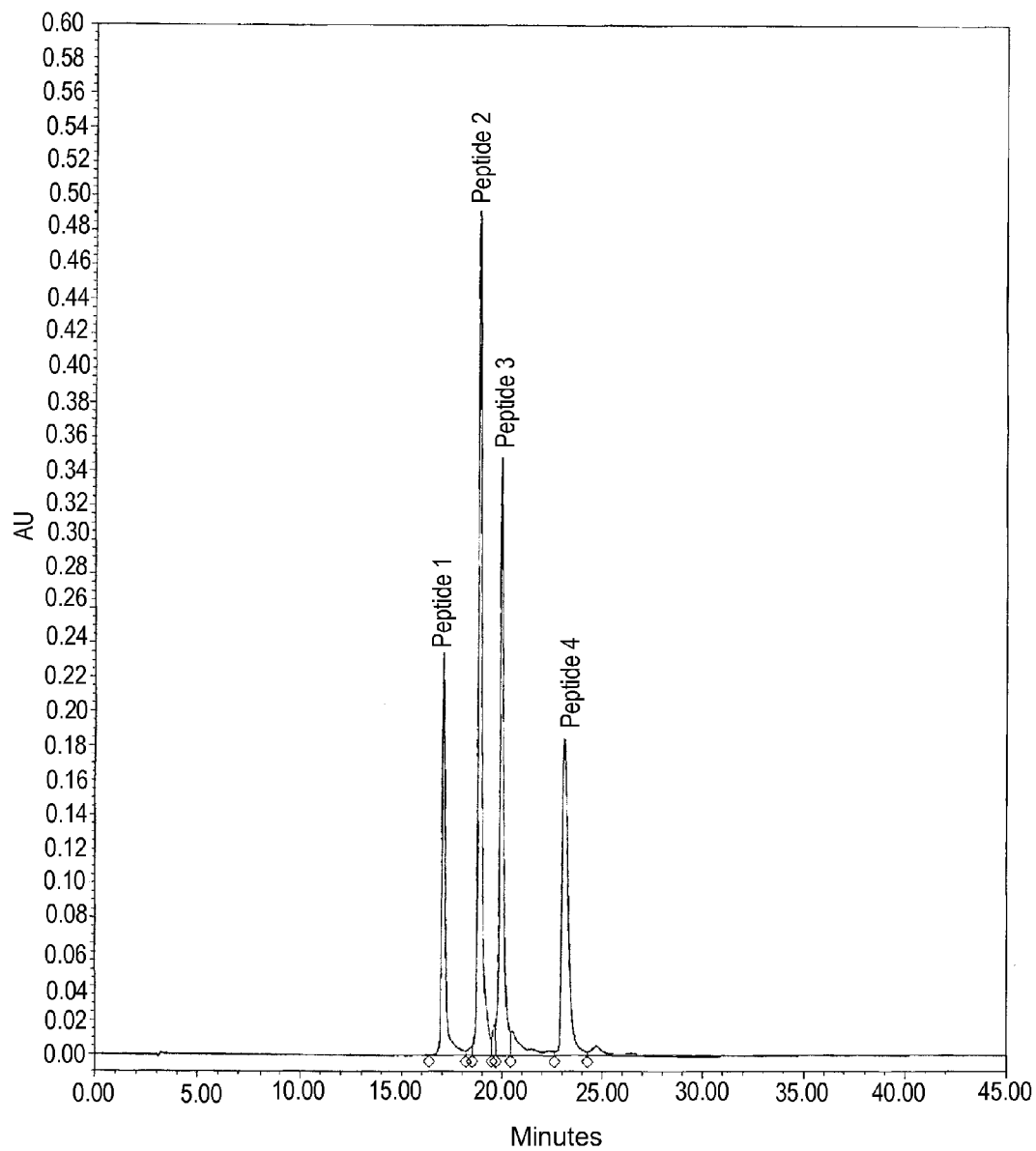
FIG. 4 depicts a high pressure liquid chromatogram of a sample of protamine sulfate analyzed by a comparative method.
Figure 5:
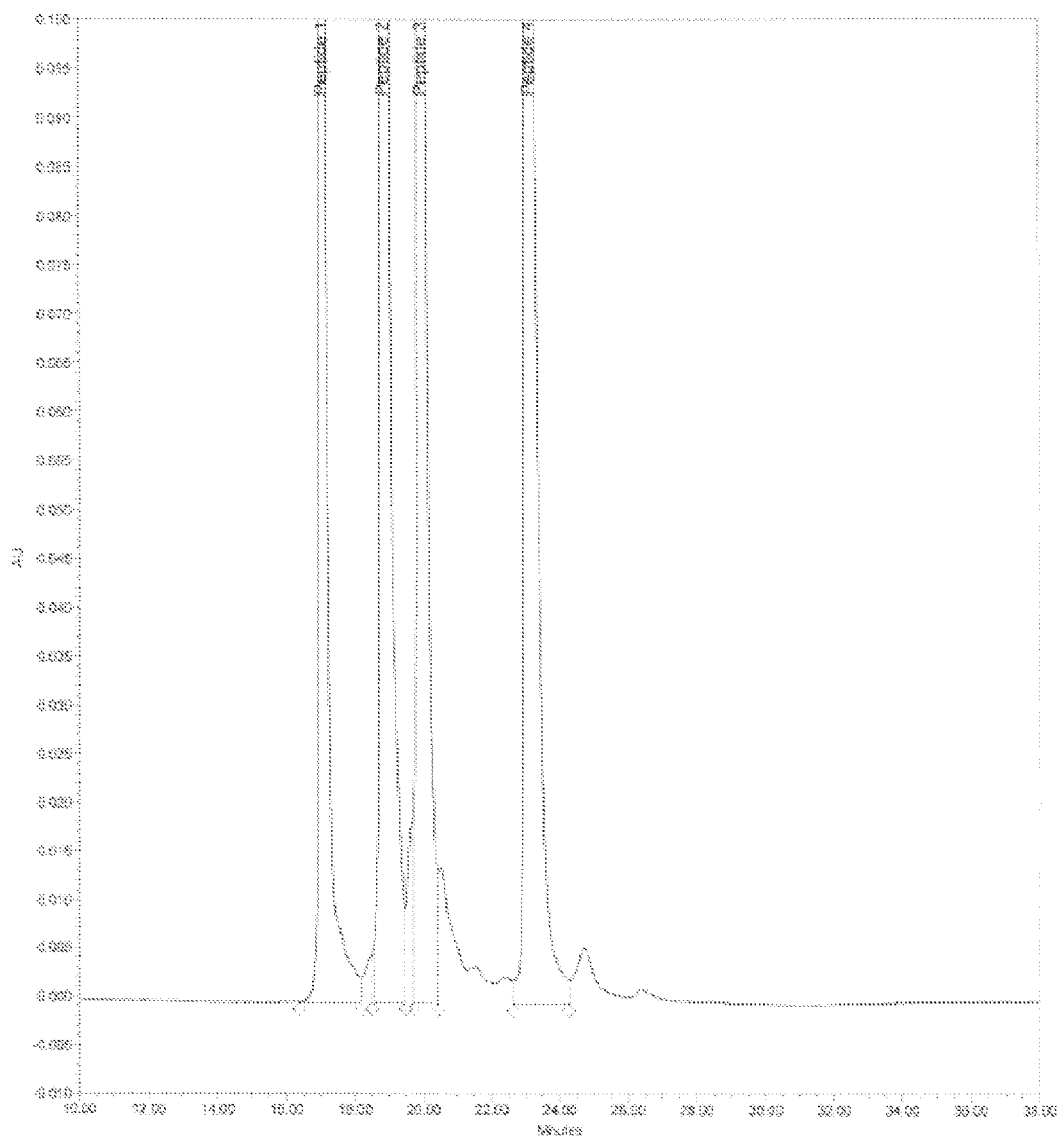
FIG. 5 depicts an expanded scale high pressure liquid chromatogram of the chromatogram depicted in FIG. 4.
Figure 6A:
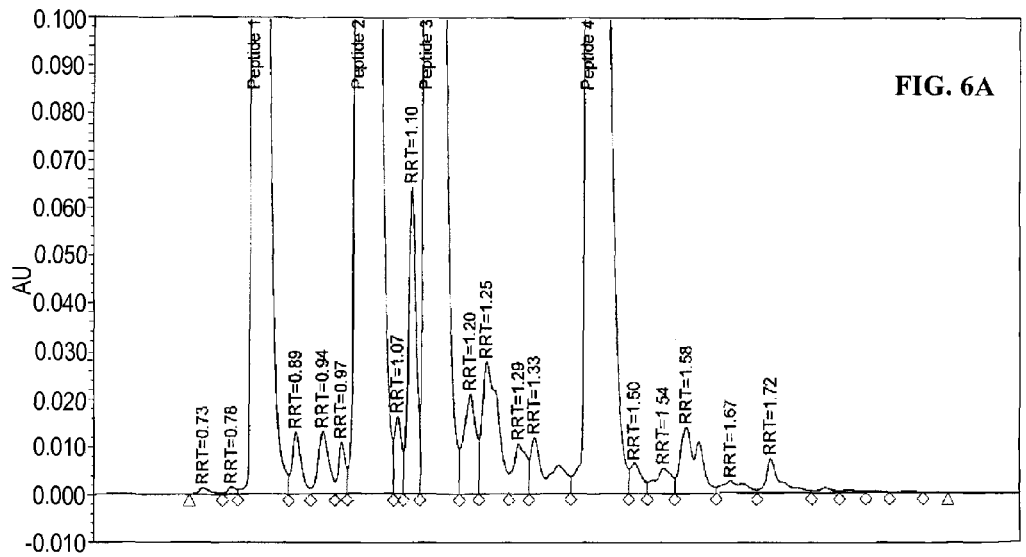
FIG. 6 depicts high pressure liquid chromatograms of a sample of protamine sulfate analyzed in accordance with an embodiment of the invention (FIG. 6A) and a comparative method (FIG. 6B).
Figure 6B:
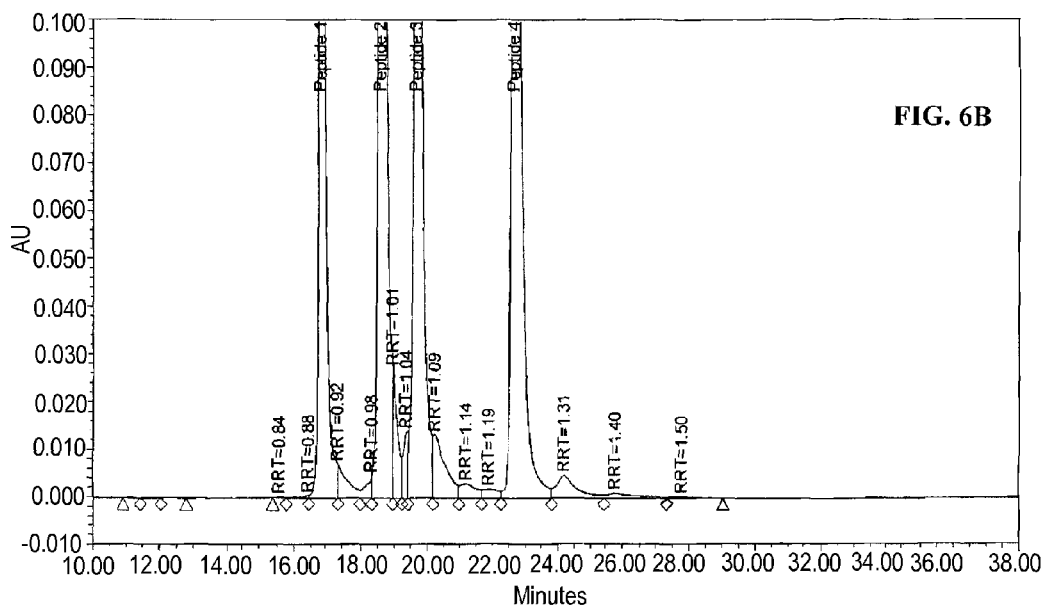

A representative full scale chromatogram of Reference Solution for protamine sulfate analyzed by the method of the present invention is provided in FIG. 1, and a corresponding expanded scale chromatogram (10 to 38 minutes) is provided in FIG. 3. A representative full scale chromatogram of Reference Solution for protamine sulfate analyzed by the comparative method is provided in FIG. 4, and a corresponding expanded scale chromatogram (10 to 38 minutes) is provided in FIG. 5. Expanded scale chromatograms (10 to 38 minutes) of a sample of protamine sulfate that were obtained by the present invention and the comparative method are provided in FIG. 6A and FIG. 6B, respectively.

The results of this example demonstrate that the method of analyzing protamine according to the invention provides enhanced sensitivity for the detection of impurities, particularly two impurities which produce HPLC peaks between the HPLC peaks corresponding to protamine major peptides 2 and 3, as compared to the comparative method.

All references, including publications, patent applications, and patents, cited herein are hereby incorporated by reference to the same extent as if each reference were individually and specifically indicated to be incorporated by reference and were set forth in its entirety herein.

The use of the terms "a" and "an" and "the" and "at least one" and similar referents in the context of describing the invention (especially in the context of the following claims) are to be construed to cover both the singular and the plural, unless otherwise indicated herein or clearly contradicted by context. The use of the term "at least one" followed by a list of one or more items (for example, "at least one of A and B") is to be construed to mean one item selected from the listed items (A or B) or any combination of two or more of the listed items (A and B), unless otherwise indicated herein or clearly contradicted by context. The terms "comprising," "having," "including," and "containing" are to be construed as open-ended terms (i.e., meaning "including, but not limited to,") unless otherwise noted. Recitation of ranges of values herein are merely intended to serve as a shorthand method of referring individually to each separate value falling within the range, unless otherwise indicated herein, and each separate value is incorporated into the specification as if it were individually recited herein. All methods described herein can be performed in any suitable order unless otherwise indicated herein or otherwise clearly contradicted by context. The use of any and all examples, or exemplary language (e.g., "such as") provided herein, is intended merely to better illuminate the invention and does not pose a limitation on the scope of the invention unless otherwise claimed. No language in the specification should be construed as indicating any non-claimed element as essential to the practice of the invention.

Preferred embodiments of this invention are described herein, including the best mode known to the inventors for carrying out the invention. Variations of those preferred embodiments may become apparent to those of ordinary skill in the art upon reading the foregoing description. The inventors expect skilled artisans to employ such variations as appropriate, and the inventors intend for the invention to be practiced otherwise than as specifically described herein. Accordingly, this invention includes all modifications and equivalents of the subject matter recited in the claims appended hereto as permitted by applicable law. Moreover, any combination of the above-described elements in all possible variations thereof is encompassed by the invention unless otherwise indicated herein or otherwise clearly contradicted by context.

The invention claimed is:

1. A method for analyzing a protamine sample for the presence or amount of at least one nucleic acid, comprising the steps of:
    (a) providing a protamine sample containing at least one nucleic acid,
    (b) subjecting the sample of protamine to disruption with trypsin to provide a first mixture, wherein the first mixture comprises trypsin, protamine, and at least one nucleic acid,
    (c) heating the first mixture under conditions sufficient to inactivate the trypsin to provide a second mixture, wherein the second mixture comprises inactivated trypsin, protamine, and at least one nucleic acid,
    (d) subjecting the second mixture to a digestion step to provide a third mixture, and (e) determining the presence or amount of at least one compound derived from the nucleic acid present in the third mixture.

2. The method of claim 1, wherein the digestion step comprises subjecting the second mixture to digestion with an endonuclease, a phosphodiesterase, an alkaline phosphatase, or combinations thereof to provide the third mixture.

3. The method of claim 1, wherein the determination comprises subjecting the third mixture to a high pressure liquid chromatography to obtain a chromatogram, and comparing a peak obtained in the chromatogram resulting from the at least one compound derived from the nucleic acid to a peak resulting from a reference standard of the at least one compound derived from the nucleic acid.

4. The method of claim 3, wherein the determination is of the presence of the at least one compound derived from the nucleic acid.

5. The method of claim 3, wherein the determination is of the amount of the at least one compound derived from the nucleic acid.

6. The method of claim 3, wherein the determination further comprises selecting a batch as a result of the determination based upon comparison to the reference standard.

7. The method of claim 1, wherein the at least one compound derived from the nucleic acid is a nucleoside.

8. The method of claim 1, wherein the protamine is protamine sulfate.

\* \* \* \* \*